United States Patent [19]
Lammintausta et al.

[11] Patent Number: 5,304,569
[45] Date of Patent: Apr. 19, 1994

[54] COMPOSITIONS AND THEIR USE IN LOWERING INTRAOCULAR PRESSURE

[75] Inventors: Risto Lammintausta, Turku; Arto Karjalainen, Oulu; Ewen MacDonald; Arto Urtti, both of Kuopio; Raimo Virtanen, Rusko, all of Finland; Thomas Yorio, Burleson, Tex.

[73] Assignee: Orion-yhtyma Oy, Espoo, Finland

[21] Appl. No.: 607,398

[22] Filed: Oct. 31, 1990

[30] Foreign Application Priority Data

Nov. 13, 1989 [GB] United Kingdom ............... 8925618
Dec. 14, 1989 [GB] United Kingdom ............... 8928288

[51] Int. Cl.$^5$ ........................................... A61K 31/415
[52] U.S. Cl. .................................. 514/396; 514/913
[58] Field of Search ............................. 514/396, 913

[56] References Cited

U.S. PATENT DOCUMENTS 4,665,085 5/1987 Coquelet et al. ................ 514/398

FOREIGN PATENT DOCUMENTS 0034473 8/1981 European Pat. Off. .
0081924 6/1983 European Pat. Off. .
0132190 1/1985 European Pat. Off. .

OTHER PUBLICATIONS

Medline 89390297 (1989), England et al.
Hodapp, Elizabeth et al, "The Effect of Topical Clonidine on Intraocular Pressure", *Arch Ophthalmol,* vol. 99 (Jul. 1981), pp. 1208-1211.
Arch. Ophthalmol. vol. 108, Sep. 1990, pp. 1264-1267, "Cardiovascular and Intraocular Pressure Effects and Plasma Concentrations of Apraclonidine", Coleman et al.
European Journal of Pharmacology, vol. 150, 1988, pp. 9-14, Elsevier Publishers B.V. (Biomedical Division) R. Virtanen et al: "Characterization of the selectivity, specificity and potency of medetomidine as an alpha2-adrenoceptor agonist".
Journal of Ocular Pharmacology, vol. 6, No. 3, 1990, pp. 251-257, Mary Ann Liebert, Inc., Publishers; D. E. Potter et al: "Review: Alpha2 and DA2 agonists as antiglaucoma agents: Comparative pharmacology and clinical potential".
Physicians' Desk Reference for Ophthamology, 16 Edition, 1988, p. 11.

*Primary Examiner*—Zohreh A. Fay
*Attorney, Agent, or Firm*—Adduci, Mastriani, Schaumberg & Schill

[57] ABSTRACT

Compounds of formula:

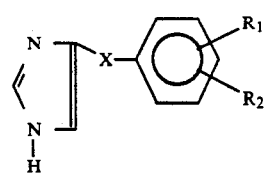

(I)

where X is —$CH_2$—, —$CH(CH_3)$—, —$CHR_3$—$CH_2$— or —$CR_3$=CH— and $R_1$, $R_2$ and $R_3$, which can be the same or different, are each H or $CH_3$ or a stereoisomer or pharmaceutically acceptable salt thereof, and pharmaceutical compositions containing them, are useful for lowering intraocular pressure in a mammal, e.g. in the treatment of glaucoma.

5 Claims, No Drawings

COMPOSITIONS AND THEIR USE IN LOWERING INTRAOCULAR PRESSURE

The present invention relates to the use of certain 4-substituted imidazoles in lowering intraocular pressure, e.g. in the treatment of glaucoma.

Glaucoma is a group of diseases characterized by an increase in intraocular pressure which causes pathological changes in the optic disk and typical defects in the field of vision. Known antiglaucoma drugs are, e.g., timolol and apraclonidine (p-aminoclonidine).

It has now been observed that imidazole derivatives of the formula:

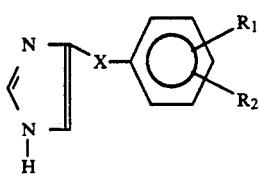

where X is $-CH_2-$, $-CH(CH_3)-$, $-CHR_3-CH_2-$ or $-CR_3=CH-$ and $R_1$, $R_2$ and $R_3$, which can be the same or different, are each H or $CH_3$, and their salts and stereoisomers are effective in lowering intraocular pressure.

The compounds of formula (I) are known, e.g. from European Patent Publication Nose. 24829, 34473, 34474 and 72615. In these publications the compounds have been described as antihypertensive agents.

The antiglaucoma activity of the compounds of formula (I) was determined by measuring the decrease of intraocular pressure (IOP) in rabbits. The tests were carried out as follows:

Adult rabbits of both sexes (weight 3–4 kg) were used in all studies. IOP was measure by tonometry using a Digilab Modular One Pneuma Tonometry following induction of a corneal anesthesia with a drop of 0.4% oxybuprocain (Oftan Obucain ®, Star, Finland). Baseline IOP was determined for both eyes at 120, 60, 30 minutes and just before topical application of the studied compounds or vehicle (control animals) on either left or right eye. The compounds were administered dissolved or suspended in a phosphate buffer, pH 6.5, at the concentration indicated in Table 1. After application IOP was determined for both eyes at 30, 60, 120, 180, 240 and 300 minutes.

The results obtained are presented in Table 1, where the maximal IOP decrease (mmHg) in response to each compound is shown. Para-aminoclonidine and timolol were studied as positive references.

The following compounds of formula (I) were tested:

| NO. | NAME |
| --- | --- |
| 1. | 4-(2,6-dimethylbenzyl)-1H-imidazole |
| 2. | 4-[2-(2,6-dimethylphenyl)ethyl]-1H-imidazole |
| 3. | 4-[2-(2,6-dimethylphenyl)ethenyl]-1H-imidazole |
| 4. | 4-[2-(2,6-dimethylphenyl)-1-methylethyl]-1H-imidazole |
| 5. | 4-[2-(2,6-dimethylphenyl)-1-methylethenyl]-1H-imidazole |
| 6. | 4-[(α-methyl)-2-methylbenzyl]-1H-imidazole |
| 7. | 4-[(α-methyl)-2,3-dimethylbenzyl]-1H-imidazole, dextro isomer |
| 8. | 4-[(α-methyl)-2,3-dimethylbenzyl]-1H-imidazole. |

TABLE 1

| Compound No. | Maximal decrease in intraocular pressure, mmHg | | Concentration and volume of drug solution dropped |
| --- | --- | --- | --- |
| | Treated eye | Contralateral eye | |
| Controls | +1.2 | −0.5 | 0 (50 μl) |
| 1. | −2.1 | −1.4 | 1 mg/ml (25 μl) |
| 2. | −1.4 | −1.4 | 5 mg/ml (50 μl) |
| 3. | −0.6 | −2.8 | 12.5 mg/ml (100 μl) |
| 4. | −1.9 | −2.1 | 2.5 mg/ml (25 μl) |
| 5. | −2.1 | −1.2 | 0.6 mg/ml (100 μl) |
| 6. | −2.4 | −2.9 | 5 mg/ml (50 μl) |
| 7. | −1.9 | −1.7 | 0.5 mg/ml (25 μl) |
| 8. | −5.9 | −5.9 | 0.2 mg/ml (50 μl) |
| p-aminoclonidine | −2.1 | −1.2 | 0.5 mg/ml (25 μl) |
| Timolol | inactive | inactive | 5 mg/ml (25 μl) |

As can be seen, the compounds of this invention are able to induce a potent decrease in IOP in rabbits. The effect can be seen in the treated and untreated (contralateral) eye. The response in the untreated eye is obviously a systemic effect due to absorption of the drug after application.

The present invention thus provides a pharmaceutical composition in a form suitable for topical application to the eye, comprising a compound of the formula:

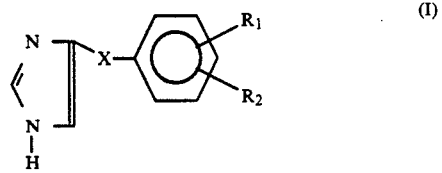

where X is $-CH_2-$, $-CH(CH_3)-$, $-CHR_3-CH_2-$ or $-CR_3=CH-$ and $R_1$, $R_2$ and $R_3$, which can be the same or different, are each H or $CH_3$, or a stereoisomer or pharmaceutically acceptable salt thereof, and a pharmaceutically acceptable carrier or diluent.

Preferably one or both of $R_1$ and $R_2$ are methyl. If the phenyl ring is mono-substituted it is preferred that the substitution is in the 2-position. If the phenyl ring is di-substituted it is preferred that the substitutions are in the 2 and 3, or 2 and 6 positions.

The compounds of the formula (I) and their stereoisomers or their pharmaceutically acceptable salts are preferably administered topically in the form of drops of a solution or suspension applied directly to the eye. Such compositions are typically sterilized aqueous solutions (i.e. eye drops) containing 0.001% to 10%, most preferably 0.005% to 1%, by weight of the active ingredient, and generally also contain a suitable buffer, stabilizer and preservative. Typical preservatives/sterilants are phenyl mercuric acetate, thimerosal, chlorobutanl, and benzalkonium chloride. Typical buffer systems are based on, for example, citrate, borate or phosphate; suitable stabilizers include glycerin and polysorbate 80.

The aqueous solutions may be formulated simply by dissolving the compound in a suitable quantity of water, adjusting the pH to about 6 to 8, making a final volume adjustment with additional water and sterilizing the preparation using methods known in the art.

The appropriate dosage of the resulting composition which should be administered will of course depend on the concentration of the drops, the condition of the subject and the individual magnitude of response to treatment. However, typical dosage ranges are about 2 to 10 drops of a 0.1% solution of active ingredient per day for an adult person.

We claim:

1. A method of lowering intraocular pressure in a mammal comprising administering to a subject in which such pressure lowering is desired, a compound of the formula:

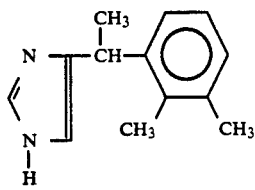

or a stereoisomer or pharmaceutically acceptable salt thereof in an amount sufficient to achieve the desired lowering in pressure.

2. The method of claim 1 in which the compound is administered to the subject in an amount equivalent to 2 to 10 drops of a 0.1% solution of compound per day.

3. The method of claim 1 used in the treatment of glaucoma.

4. The method of claim 1 in which the compound is 4-[(α-methyl)-2,3-dimethylbenzyl]-1H-imidazole.

5. The method of claim 4 in which the compound is the dextro isomer.

* * * * *